(12) United States Patent
Hoernig

(10) Patent No.: US 8,338,810 B2
(45) Date of Patent: Dec. 25, 2012

(54) RADIATION PROTECTION WALL FOR MAMMOGRAPHY SYSTEMS WITH INTEGRATED USER INTERFACE

(75) Inventor: Mathias Hoernig, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 13/213,299

(22) Filed: Aug. 19, 2011

(65) Prior Publication Data

US 2012/0051520 A1 Mar. 1, 2012

(30) Foreign Application Priority Data

Aug. 31, 2010 (DE) .......................... 10 2010 035 917

(51) Int. Cl.
*H05G 1/64* (2006.01)
*B23P 11/00* (2006.01)
(52) U.S. Cl. .................... 250/515.1; 250/505.1; 378/37; 378/203; 378/16; 378/65; 378/87
(58) Field of Classification Search ............... 250/505.1, 250/515.1, 516.1, 517.1, 519.1, 526; 378/16, 378/37, 51, 62–65, 87, 167, 189, 193–198, 378/203, 210
See application file for complete search history.

(56) References Cited

U.S. PATENT DOCUMENTS

| 4,965,456 | A | 10/1990 | Huettenrauch et al. |
| 6,448,571 | B1 * | 9/2002 | Goldstein .................. 250/515.1 |
| 7,648,273 | B2 | 1/2010 | Manzke et al. |
| 2003/0091152 | A1 | 5/2003 | Dietz et al. |
| 2004/0202280 | A1 | 10/2004 | Besson |
| 2008/0217564 | A1 | 9/2008 | Beyar et al. |

* cited by examiner

*Primary Examiner* — Bernard E Souw
(74) *Attorney, Agent, or Firm* — Schiff Hardin LLP

(57) ABSTRACT

In a mammography system with a radiation protection wall, a production method for a radiation protection wall, and a method to operate a mammography system, the radiation protection wall has a further function in addition to the radiation protection. The radiation protection wall additionally serves to present a user interface of a control program to control the mammography apparatus, and can still display the images acquired by the mammography apparatus. The display region of the radiation protection wall is provided in the upper region of said radiation protection wall and can be fashioned as a touchscreen in order to control the mammography apparatus with the detected touch signals.

18 Claims, 3 Drawing Sheets

RADIATION PROTECTION WALL FOR MAMMOGRAPHY SYSTEMS WITH INTEGRATED USER INTERFACE

BACKGROUND OF THE INVENTION

1. Field of the Invention

The present invention concerns medical mammography systems and in particular concerns a radiation protection wall for a mammography system.

2. Description of the Prior Art

Digital mammography systems according to the prior art include the acquisition apparatus for the mammogram and a radiation protection wall in order to offer effective protection against ionizing radiation, for example in the electromagnetic spectrum of the x-ray system. The radiation protection wall is produced from transparent, smoothed and polarized lead glass. The radiation protection wall of known systems can be integrated into a computer-based workstation. The computer-based workstation (acquisition workstation—AWS) normally includes a computer (as a local workstation, with or without a network connection), a monitor, and a keyboard, as well as additional peripheral devices (mouse, printer etc., for example) as necessary. The individual electronic elements or devices of the workstation are normally integrated into a mount, frame and/or into a carrier.

FIG. 1 shows a typical design of a mammography system with a workstation into which a radiation protection wall is integrated. A user of the workstation (normally an MTRA—medical technology radiology assistant) operates the mammography system from behind the radiation protection wall of the workstation. For this purpose, the user must keep both the patient at the mammography apparatus and the monitor of the workstation in sight to control the mammography process. In FIG. 1 an angle range is indicated as an example that denotes in what viewing angle range the user must be active in the control of the mammography process. In systems according to the prior art this is relatively large. Moreover, for an error-free implementation of the medical examination process it is necessary for the user at the workstation to observe the patient at the mammography apparatus without interruption. However, the user must simultaneously and additionally operate the computer of the workstation to control the mammography process, that diverts the user from the continuous observation of the patient, however. The diversion is in particular more severe when the user must assume a different position for the operation and must significantly vary the viewing angle.

SUMMARY OF THE INVENTION

An object of the present invention is to provide an improved radiation protection wall for medical technology apparatuses. In particular, the safety in the operation of the mammography system should be increased and the operation for the user should be facilitated. Since previous radiation-protected workstations are normally very heavy and cumbersome due to the plurality of integrated electronic elements, the present invention moreover has posed the object of providing a more slender and easily manipulable radiation-protected workstation that in particular can more easily be moved in the examination room. The electronic components that have previously been provided as an individual, separate module—in particular the monitor and if necessary the keyboard as well—should also be integrated into the radiation protection wall, such that these can be omitted.

A basis of the present invention is to expand a radiation protection wall in terms of its function, such that it serves not only for radiation protection but also performs a display and control function.

For this purpose, the invention provides a radiation protection wall that has a radiation protection region that is produced from a radiation protection material, and the radiation protection wall has a further functionality in addition to radiation protection, namely a display functionality to show digital contents, and in particular a user interface or a section of the user interface of an apparatus control program. Moreover, the radiation protection wall—in particular the display region—can also be fashioned as a touchscreen in order to be able to control the apparatus on or at the radiation protection wall, so to speak.

The radiation protection wall serves for use in technical apparatuses that emit ionizing radiation. A preferred embodiment of the present invention relates to medical technology applications. Alternatively, however, the invention can be related to arbitrarily different technical applications (for example production manufacturing of apparatuses by means of x-ray-based methods; protection systems in the radioscopy of subjects or bodies, for example in airport monitoring systems or other technical systems that require a radiation protection). In the field of medical technology, applications exist for radiation protection walls in the field of cardiology, radiology (such as computer tomography), mammography, urology or surgery. The radiation protection wall according to the invention is characterized by a high protective effect against ionizing radiation in the electromagnetic frequency range, and by a switchable display function that advantageously can be activated and deactivated. The display function relates to the presentation of a display. An interface of a connected computer is typically presented on the display.

Depending on the application or depending on the medical technology apparatus, the radiation protection wall can be permanently integrated into a separation wall (wall or door etc.). Alternatively it can be integrated into a mobile, computer-based control panel. Additional embodiments concern the use of the radiation protection wall as an individual element, or the integration of the radiation protection wall into additional elements of a comprehensive technical system.

In a preferred embodiment, the medical technology apparatus is a digital mammography apparatus. Such an apparatus is normally controlled via a computer-based control panel. In particular, here the movement of the compression surface is controlled relative to the detector, the adjustment of the field of view (FOV), the degree of the compression, the triggering of the x-ray radiation, etc. The control of the mammography apparatus is normally taken over by a user (normally an MTRA) who is located either in a separate control room that is separated from the examination room by a radiation protection wall, or the operator is protected from the radiation by a movable radiation protection wall. The control panel includes a computer, a monitor, a keyboard and possibly additional input/output interfaces for user interaction (mouse etc., for example). Instead of a local computer, it can also be provided to merely provide an interface to a central server. All electronic devices (monitor, keyboard, computer etc.) are typically accommodated as separate elements in a frame-like arrangement. The frame-like arrangement comprises the radiation protection wall. As an alternative, the frame-like arrangement can also be fashioned flat, with a region of the surface being formed by the radiation protection wall. It should be noted that size, shape, material and embodiment of the radiation protection wall can be arbitrarily configured for the invention, such that pluggable rack system-like modules or modules made of plastic and glass can also be combined, for example.

The primary embodiment concerns mammography apparatuses or other medical technology apparatuses that likewise emit ionizing x-rays, such that the radiation protection material comprises lead glass. Alternatively, it is possible to apply the invention to other technical apparatuses that likewise require a radiation protection (not necessarily x-rays but rather radiation in other wavelengths).

A significant core idea of the invention is apparent in that the radiation protection wall has at least one display region; multiple separate display regions can also be provided for the same or different functions (for example display of the interface of the control program and display of the acquired image data—with the same function, namely display—and touchscreen for user interaction in the control of the mammography apparatus—with a different function, namely touchscreen). Furthermore, it is not necessary that the display region spans across the entire extent of the radiation protection wall. The display region is advantageously located within the field of view of a user in the operation of the control panel. The display region serves to present arbitrary digital contents and for this is advantageously connected (in terms of data) wirelessly or via a cable with a computer-based instance, or directly with the control panel.

The display region typically serves to present a user interface (or a section of the same) of the control program for the medical technology apparatus. Depending on the use, the display region can also serve to present additional elements. For example, for the clinical workflow it has proven particularly advantageous when, in addition to the user interface of the control program, the image sequences acquired with the mammography apparatus are also shown. This has the advantage that the operator immediately receives feedback of the settings the user has made to control the medical technology apparatus and can modify the control again if necessary. A regulation mechanism is inasmuch provided for this that enables a modified control of the medical technology apparatus.

In complex applications, the control program that is executed at the control panel [sic], which leads to the situation that the associated user interface has many presentation examination subject. In a preferred embodiment, it is therefore provided that not all presentation elements of the user interface are shown on the display region of the radiation protection wall, but rather only selected, relevant elements. It is likewise possible to show additional elements in the display region, for example reference exposures of the patient for comparison or standard settings for operation of the mammography apparatus.

According to the invention, multiple variants are provided for the design of the display region of the radiation protection wall, which variants can also be used in combination and that also can be expanded by additional technologies for touchscreens. These are:

1. The display function of the display region is executed via projection of the data to be presented onto the display region (for example by means of a projector that can likewise be part of the radiation projection system).

2. The display function is provided by providing a touchscreen region with integrated sensor technology on the radiation protection wall or on a display region of the radiation protection wall, wherein interfaces are provided between the display region and the computer-based control panel.

2a. The touchscreen region is provided by an integrated LED field or TFT field with corresponding connections or, respectively, interfaces to a computer.

2b. The touchscreen region is formed by a thin, transparent coating (for example a display film) that is applied on the display region (for example OLED, organic light emitting diode).

In all embodiments the interfaces between display region and computer can be executed via cables or wirelessly (for example Bluetooth, WLAN, LAN etc.).

The technology for the design of the touchscreen is not limited in principle and comprises a capacitive, optical, surface wave-based or infrared light-based technique.

Moreover, it is possible to activate and deactivate the display functionality of the radiation protection wall selectively via a user interaction. It is likewise possible to make pre-adjustments here so that an activation of the display functionality is also executed automatically given activation of the control program. The display functionality can be confirmed as needed via a confirmation signal of the user before it is activated.

It is advantageously pre-set that, given a deactivated display functionality, the radiation protection wall in the display region is transparent in order to allow a free view of the mammography apparatus with patient.

With reference to the possibilities mentioned in the preceding to design the display functionality, referring to the first embodiment by means of a projection it is noted that the intensity (brightness) of a projection means (projector, for example) is automatically adapted to the degree of transparency of the radiation protection wall in order to achieve as optimal an illumination situation as possible.

According to a further advantageous embodiment it is provided that the radiation protection wall comprises at least one additional functionality—advantageously an operating functionality—in addition to the display functionality. In particular, a virtual or real keyboard via which the user can make inputs can be integrated into the radiation protection wall. This can take place in the form of a film keyboard, for example, as it is known in mobile telephone keyboards. As an alternative to the finger-position detection, an operating element (pin, for example) can also be provided for user input. In order to make it possible that there be no further repositioning for the user and to make a fast operation of the system possible, a virtual or real QWERTY keyboard is normally provided on the radiation protection wall, which keyboard typically replaces the previous physical keyboard and the mouse. This has the advantage that the control panel can be fashioned to be significantly thinner and comprises fewer electronic elements. In the preferred embodiment the radiation protection wall can in fact merely be fashioned as a (mobile) wall into which is integrated the radiation protection wall according to the invention with display and/or input/output functionality. The radiation protection wall also no longer needs to be a separate computer; rather an interface or, respectively, an interface module (adapter) to a network or a server can merely be provided for this.

So that the operator can also make written notes during the mammography process, in addition to the vertically arranged radiation protection element it has proven to be reasonable in practice to additionally fashion the radiation protection wall additionally [sic] with a horizontal tray element that serves as a support for writing or to hold additional electronic devices (for example the keyboard or the mouse in the event that these are not integrated into the radiation protection wall).

In the preferred embodiment, the radiation protection wall according to the invention no longer comprises a separate monitor. The display functionality is completely integrated into the radiation protection wall so that the additional provision of a monitor is superfluous. The additional electronic elements (keyboard, computer, foot operation pedal etc., for example) can likewise be integrated individually and selectively into the radiation protection wall. However, this is not absolute necessary, such that the most different embodiments of the radiation protection wall with respective integrated elements should be encompassed by the protective scope of this Application.

The size, shape and position of the display region on the radiation protection wall can be varied arbitrarily depending on the use and intended purpose. According to a preferred embodiment, the configuration and also a variation of the display region (among other things with regard to the parameters cited in the preceding, such as size, position and shape) are also possible during use, and in particular during a mammography process or, respectively, given a finished radiation protection wall. This represents an important advantage relative to systems from the prior art since the radiation protection wall according to the invention can also still be configured at the installation location, and thus after manufacturing. Configuration possibilities pertain to the adjustment of the display region, in particular settings of the touchscreen, settings with regard to the virtual keyboard and transparency settings of the radiation protection wall. In particular, it is provided that a degree of transparency can be adjusted continuously [with infinite variability].

Through the configuration and adjustment possibilities the significant advantage arises that the radiation protection wall according the invention can also be adapted to the respective application after its production, and thus in a clinical use. For example, if a radiation protection wall according to the invention should be used in a very spatially limited clinical application, which radiation protection wall has an integrated display region that additionally has a separate keyboard and a separate mouse, it is thus possible to reconfigure the radiation protection wall so that said radiation protection wall comprises only a vertical element, and the previously horizontally projecting tray can be dismounted. For example, the new configuration then enables the keyboard (and advantageously additional user interface interfaces) to likewise be integrated into the radiation protection wall. Moreover, only an interface to the server or to a network can be provided as a replacement for the local computer. After this application the radiation protection wall can again be refitted by a few handles into the known shape of a radiation protection wall with horizontal tray. For simple and fast refitting capability, all elements of the radiation protection wall according to the invention are fashioned to be of modular design with corresponding standardized interfaces that enable a fast exchange and swapping of the elements.

In order to produce an optimal exposure situation in the examination room, in a preferred embodiment of the invention it is provided that the radiation protection wall additionally comprises an interface to control the room illumination. An action field via which the room illumination is regulated—in particular dimmed—can be integrated into the radiation protection wall (in particular into the touchscreen region of the radiation protection wall). Moreover, additional activation fields are integrated into the radiation protection wall, via which additional activation fields the user can make additional adjustments, for example the transparency of the radiation protection wall, the activation or deactivation of the display function, zoom capabilities for the individually shown elements or, respectively, arrangement possibilities for icons and elements on the display region of the radiation protection wall. Moreover, a triggering element is provided that represents the previous radiation triggering button and is designated to trigger the x-ray radiation of the mammography apparatus. Moreover, in an additional advantageous embodiment a hardware emergency off button (that can be fashioned as a virtual switch on the touchscreen region of the radiation protection wall) is provided in order to be able to trigger an emergency stop of the mammography system.

A particular advantage is that, according to the invention, the monitor and/or a separate keyboard at the workstation of the mammography apparatus can be omitted in that the radiation protection wall comprises a display region and/or a touchscreen region. Different touchscreen systems known in the prior art can thereby be used, advantageously multitouch systems as well in order to enable an efficient control of the mammography process by detecting multiple simultaneous activations on the touch-sensitive field.

The different, alternative embodiments of the radiation protection system and of the radiation protection wall that are mentioned in the preceding are also to be applicable to the production method for the radiation protection wall and the method to operate the medical technology apparatus.

The above object is furthermore achieved by a radiation protection wall that additionally has a display functionality and/or a touchscreen functionality as described above.

The invention thus also encompasses a production method for such a radiation protection wall and a method to operate the medical technology apparatus (in particular the mammography apparatus) at the computer-based control panel that is integrated into the radiation protection wall described above.

DESCRIPTION OF THE PREFERRED EMBODIMENTS

Figure 1:
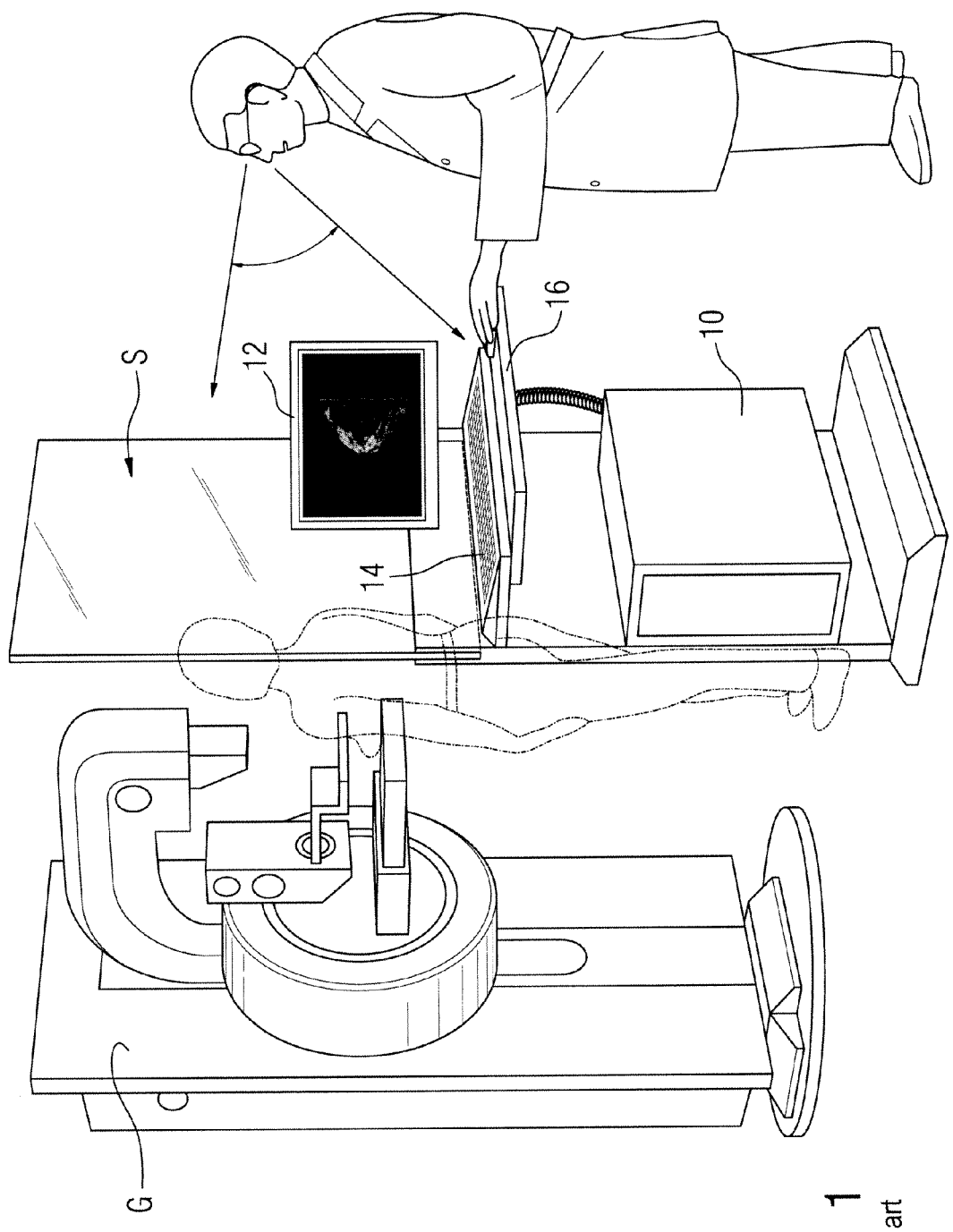
FIG. 1 is an overview depiction of a known mammography system from the prior art.
Figure 2:
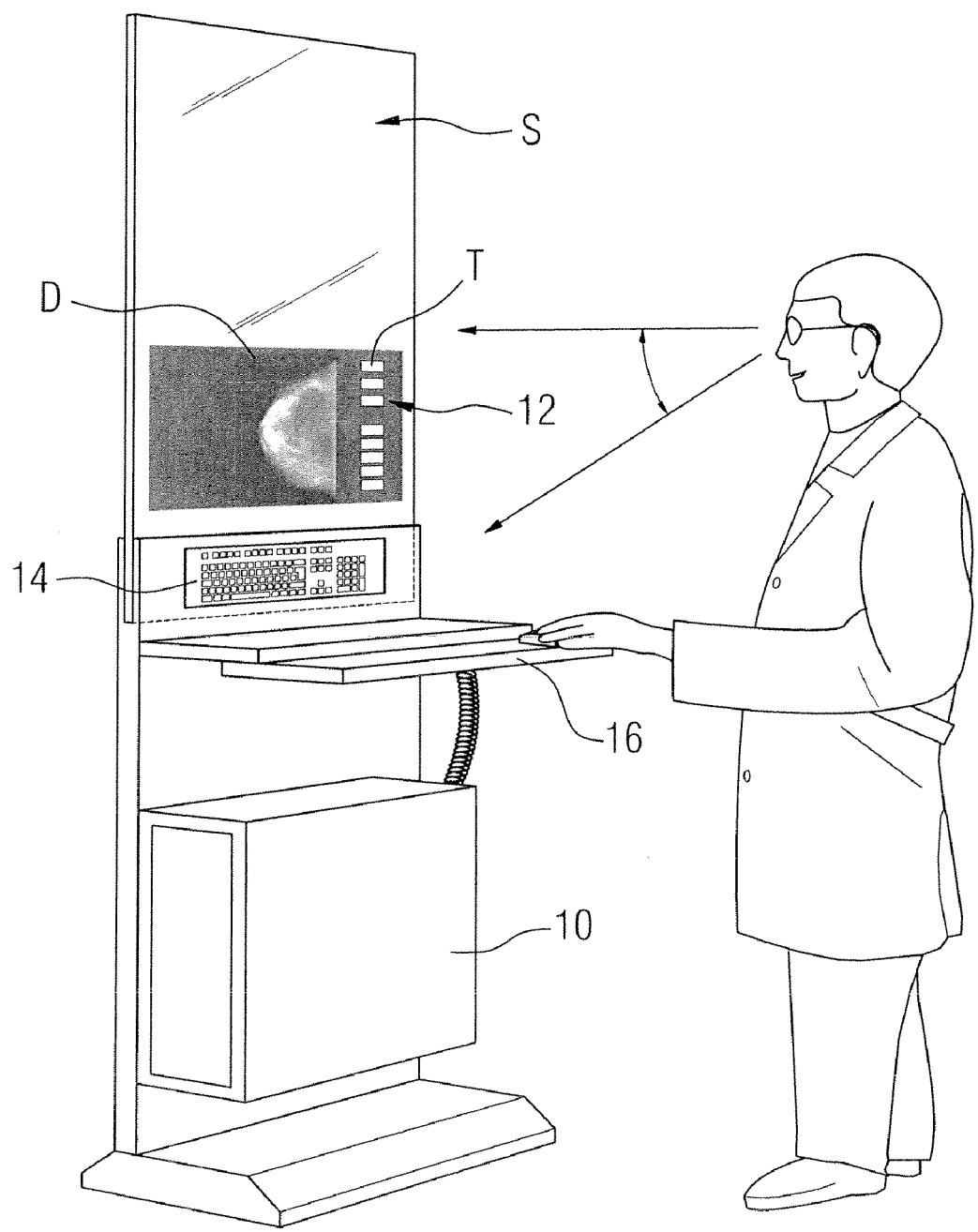
FIG. 2 is an overview depiction of a known mammography system according to a preferred embodiment of the invention.

With reference to FIG. 2 an embodiment of the present invention is described in the form of a radiation protection wall S of a medical system. The primary embodiment concerns medical technology apparatuses, in particular mammography apparatuses G. This is presented as an example of the prior art in FIG. 1. The mammography apparatus G is engaged in data exchange with a computer-based control panel that is shown both in FIG. 1 and on the right side in FIGS. 2 and 3. The control panel is computer-based and typically comprises a local computer 10 and, in the prior art (see FIG. 1), a separate keyboard 14 and a separate monitor 12, as well as possible additional input/output apparatuses that are arranged at the radiation protection wall S. The radiation protection wall S is advantageously provided with a protruding mount 16 that serves as a tray for the monitor 12 and the keyboard 14.

The radiation protection wall S has multiple elements and is in particular fashioned in the upper area with a radiation protection region that is produced from a radiation protection material, in particular lead glass. In the prior art the radiation protection region is fashioned to be transparent in order to allow the operator who works at the control panel an uninterrupted view of the patient at the mammography apparatus G.

Figure 3:
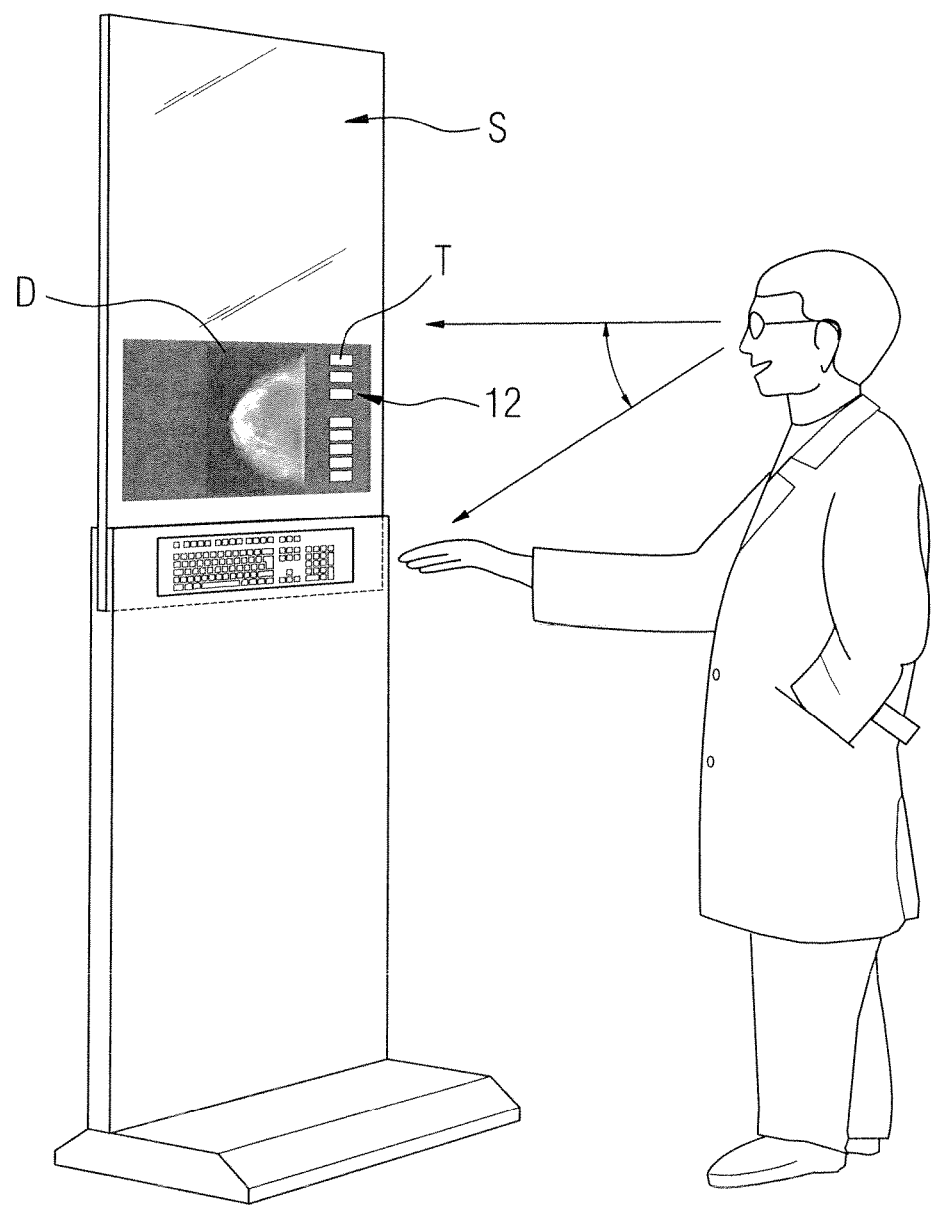
FIG. 3 shows an alternative embodiment of the radiation protection wall according to the invention as depicted in FIG. 2.

The solution according to the invention, in which the radiation protection wall S not only takes over the function of radiation protection but moreover contains a display function, is shown in FIGS. 2 and 3. A control program that runs on the computer 10 to control the mammography apparatus G was previously operated with the additional input and output devices via the monitor in the prior art. According to the invention, these user interfaces for operation of the control program are now integrated into the radiation protection wall S.

In FIG. 2 the radiation protection wall S is designed with a display region D to display digital data and a touchscreen region T to operate the computer 10 or, respectively, to control the mammography apparatus G by means of the control program, on which display region D and touchscreen region T the interface of the control program is depicted with respective operating elements of the interface, so to speak.

Similar to the prior art, the radiation protection wall in the embodiment shown in FIG. 2 thus includes the vertical wall into which a radiation protection region is integrated in the upper area. The display region D and the touchscreen region T are integrated into the radiation protection region. In the example shown in FIG. 2 the touchscreen region T comprises two regions: a vertically extending region that can be arranged next to the display region and graphical activation elements for activation of the user interface. The vertical region shown in FIGS. 2 and 3 is also designed to display meta-information regarding the acquired images. A horizontally extending second region is arranged below the display region and represents a virtual keyboard that should replace the real one. Moreover, the radiation protection wall S in the example of FIG. 2 additionally includes the retention device 16 as a tray and the computer 10, as well as a foot element. Rollers can be integrated into the foot element in order to design the radiation protection wall so that it is mobile or, respectively, movable.

In FIG. 2 the arrows should identify a viewing direction of the operator during the operation of the mammography apparatus G. In the operation of the mammography apparatus G the operator must look back and forth between the presentation of the control program on the display region G and the person to be examined at the mammography apparatus G. The different viewing angles that the person most adopt are identified with the arrows in FIG. 2. If the angle range of the solution according to the invention is compared with the angle range according to the prior art (FIG. 1), it is clear that the angle range of the solution according to the invention is significantly smaller, such that the operator must vary the viewing angle only very slightly between apparatus G and display D. The operator can thus maintain a preferred viewing direction, which in particular leads to an improved ergonomics and furthermore leads to the situation that the safety of the medical examination can be improved since a continuous and persistent monitoring of the person at the mammography apparatus G can be ensured.

The radiation protection wall S according to the invention is modular in design, such that its elements can also be arbitrarily varied, combined an reconfigured in use.

It is thus possible that the radiation protection wall S in an extremely thin embodiment (that is presented as an example in FIG. 3) comprises only a vertical wall or a vertical stand into which the radiation protection wall S is integrated. The horizontally projecting mount 16 is no longer contained in this embodiment. The computer 10 is likewise absent. Only an interface to a network or to a central server (which is not shown in any further detail in FIG. 3) is provided. Moreover, the keyboard 14 is also integrated into the radiation protection wall. The display region D advantageously extends across the total width of the radiation protection wall S and nearly across the entire height, wherein the typical format of the monitor 12 (width times height) was maintained. The region of the radiation protection wall S that is not overlaid by the display region or the touchscreen region T can be configured in an additional advantageous embodiment of the invention. In particular, the transparency and the size of this region can be selected here. It is preset that the remaining region that is not designated for the presentation of data remains transparent in order to continue to enable the view of the patient.

In a further embodiment not only the surface of the control program, but also the image sequences acquired by the mammography apparatus G, are presented in the display region D on the radiation protection wall. The size, shape and at which position the acquired image data are shown can be configured.

One advantage of the solution according to the invention results in that the presentation of the images can be executed at a significantly larger size since the display region D is significantly larger than the monitors 12 provided in the prior art. Furthermore, the graphical presentation with regard to the illumination can optimally be adapted to the respective application. In particular, it is possible that the background for the display region D and/or for the touchscreen T of the radiation protection wall S can be configured, and in particular can be switched to black.

One significant advantage is also apparent in the fundamental configuration capability of the radiation protection wall S according to the invention. It can advantageously be configured by the user whether the display functionality and/or the touchscreen functionality of the radiation protection wall S should be connected or not. In other words, the user can select whether he would like to work with the conventional radiation protection wall S from the prior art, with a separate monitor and a keyboard 14, or whether he would like to use the display functionality and/or the touchscreen functionality of the radiation protection wall S.

Due to the modularity of the radiation protection wall S it is possible to arbitrarily configure the design of the radiation protection wall S so that, in the simplest version, it comprises only a vertical wall S (as shown in FIG. 3, for example), or it can be executed as in the prior art with regard to the structural embodiment and comprise a computer 10 and a mount 16 on which a keyboard 14 can be placed so that the radiation protection wall S according to the invention in this exemplary embodiment differs from the prior art only in that no separate monitor 12 is provided. The display function is completely integrated into the radiation protection wall S. It is important that an activation element that is designed to activate the medical technology apparatus is always provided in the radiation protection wall S. In the event that the medical technology apparatus G is a mammography apparatus, here the triggering of the x-ray radiation can be initiated. Moreover, the radiation protection wall S comprises an emergency off element with which the medical technology apparatus can immediately undergo an emergency shutdown. These elements (activation element and emergency off element) can also be integrated as additional icons into the display region D. In more complex exemplary embodiments, the radiation protection wall S can additionally comprise further functions and, for example, control the room illumination in that an interface with the light fixtures is provided in order to dim these, for example. Depending on the application, additional electrical or electronic apparatuses can be controlled at the radiation protection wall S, for example loudspeakers via which acoustic information (positioning instructions for the patient, for example) can be applied.

Due to the modularity of the radiation protection wall S, an additional advantage is apparent in that the individual elements of the radiation protection wall S can also be arranged and be provided independent of one another and separately, so to speak. For example, the computer 10 of the control panel can be accommodated in a different room or at a different position than the mammography apparatus G or than the radiation protection wall S. The respective elements can be moved independent of one another.

In an alternative embodiment, additional operating elements can also be arranged at a foot part of the radiation protection wall S. In particular, switching elements that can assume only two states (for example a radiation triggering element or a hardware emergency off switch) are suitable for this.

Depending on the embodiment, the display region D can be used only to present or, respectively, display information. Alternatively, it can also be fashioned to be touch-sensitive in order (as a touchscreen) to also translate inputs of the user into control commands for the mammography apparatus G or other electronic or electrical elements (the lighting, for example).

In order to optimize the data in the display region D, additional configuration possibilities are provided that are arranged in the form of additional elements on the radiation protection wall S to adjust the display (for example resolution, size, position, additional presentation details such as color, contrast, brightness etc.).

Although modifications and changes may be suggested by those skilled in the art, it is the intention of the inventor to embody within the patent warranted hereon all changes and modifications as reasonably and properly come within the scope of his contribution to the art.

I claim as my invention:

1. A radiation protection system for a medical technology apparatus, said medical technology apparatus comprising a source of penetrating radiation, said radiation protection system comprising:
   a computer configured to operate said medical technology apparatus according to a control program that includes a display functionality;
   a radiation protection wall comprising a radiation protection region comprised of material that is substantially impenetrable by said penetrating radiation, said radiation protection wall having a first side configured to face said source of penetrating radiation and a second side opposite to said first side; and
   said radiation protection wall being configured to communicate with said computer to implement said display functionality by presenting a display generated by said computer program at said second side of said radiation protection wall.

2. A radiation protection system as claimed in claim 1 wherein said material comprises leaded glass.

3. A radiation protection system as claimed in claim 1 wherein said radiation protection wall is configured to implement said display functionality to present a display, at said second side, of at least one of a user interface that operates said control program, and an image acquired by said medical technology apparatus using said penetrating radiation source.

4. A radiation protection system as claimed in claim 1 wherein said radiation protection wall is configured to implement said display functionality by generating a visual projection of said display at said second side of said radiation protection wall.

5. A radiation protection system as claimed in claim 4 wherein said radiation protection wall comprises a predetermined display region in which said visual projection is projected.

6. A radiation protection system as claimed in claim 1 wherein said radiation protection wall is configured to implement said display functionality by displaying a touchscreen designed to operate said control program, and wherein said radiation wall comprises a sensor system integrated therein correlated with the displayed touchscreen.

7. A radiation protection system as claimed in claim 6 wherein said radiation protection wall comprises a predetermined display region in which said sensor system is integrated and at which said touchscreen is displayed.

8. A radiation protection system as claimed in claim 6 wherein said integrated sensor system comprises sensors selected from the group consisting of capacitive sensors, resistive sensors, optical sensors, surface wave-sensitive sensors, and infrared light-sensitive sensors.

9. A radiation protection system as claimed in claim 1 wherein said radiation wall comprises a display region at which said display functionality is implemented, and being manually operable activation/deactivation element configured to, when manually operated to activate said display functionality, causes said display to be presented in said display region, and when manually operated to deactivate said display functionality, causes said display region to be transparent.

10. A radiation protection system as claimed in claim 1 wherein said computer comprises a keyboard integrated into said radiation protection wall.

11. A radiation protection system as claimed in claim 1 wherein said radiation protection wall comprises a wall region having a transparency allowing said medical technology apparatus to be seen through said wall region, and wherein said radiation protection wall is configured to allow a degree of said transparency to be selectively adjusted.

12. A radiation protection system as claimed in claim 1 wherein said radiation protection wall is configured to implement said display functionality by displaying a graphical user interface for said control program that includes at least one of an activation element that activates said medical technology apparatus, and an emergency stop element that immediately stops operation of said medical technology apparatus.

13. A radiation protection system as claimed in claim 1 wherein said computer program is configured to operate said computer to control said medical technology apparatus as a mammography apparatus.

14. A radiation protection wall for use with a medical technology apparatus comprising a source of penetrating radiation, said radiation protection wall comprising:
   a radiation protection region comprised of material that is substantially impenetrable by said penetrating radiation; and
   electronics built into said radiation wall that are configured to present a display associated with operation of said medical technology apparatus.

15. A method for producing a radiation protection wall for a medical technology apparatus comprising:
   providing a radiation protection wall with a radiation protection region comprised of material that is substantially impenetrable to said penetrating radiation; and
   embodying a display functionality in said radiation protection wall for a control program of a computer that operates said medical apparatus according to said control program, said display functionality allowing display at said radiation protection wall of at least a portion of a user interface of said control program.

16. A method as claimed in claim 15 comprising integrating a display field into said radiation protection wall, and providing said display field with a hard-wired or wireless configuration to serve as said interface.

17. A method as claimed in claim 15 comprising applying a display film to said radiation protection wall and providing said display film with a hard-wired or wireless configuration to serve as said interface.

18. A method for operating a medical technology apparatus comprising a source of penetrating radiation, said method comprising:
   operating said medical technology apparatus from a computer according to a control program that includes a display functionality;
   protecting a user of said computer against radiation from said source of penetrating radiation by interposing a radiation protection wall, comprising a radiation protection region comprised of material that is substantially impenetrable by said penetrating radiation, between said source and said user, said radiation protection wall having a first side configured to face said source of penetrating radiation and a second side opposite to said first side; and
   with electronics built into said radiation protection wall being, communicating with said computer to implement said display functionality by presenting a display generated by said computer program at said second side of said radiation protection wall.

* * * * *